United States Patent [19]

Daniels

[11] Patent Number: 4,784,889
[45] Date of Patent: Nov. 15, 1988

[54] PRISONER LEG RESTRAINT

[76] Inventor: Jerry Daniels, 4308 Ooltewah-Ringgold Rd., Ooltewah, Tenn. 37363

[21] Appl. No.: 68,020

[22] Filed: Jun. 30, 1987

Related U.S. Application Data

[63] Continuation-in-part of Ser. No. 2,212, Jan. 12, 1987, Pat. No. 4,728,553, which is a continuation-in-part of Ser. No. 803,650, Feb. 12, 1985, Pat. No. 4,643,932.

[51] Int. Cl.⁴ .................. A62B 35/00; B60R 22/00
[52] U.S. Cl. ............................... 428/100; 128/876; 297/466; 428/900
[58] Field of Search .............. 428/100, 900; 128/134; 297/466

[56] References Cited

U.S. PATENT DOCUMENTS

| | | | |
|---|---|---|---|
| 3,307,872 | 3/1967 | Murcott | 297/468 |
| 3,321,455 | 5/1967 | Christen | 428/98 X |
| 3,529,865 | 9/1970 | Atwell | 428/181 X |
| 3,939,829 | 2/1976 | Spann | 128/80 R X |
| 3,992,057 | 11/1976 | Studebaker | 297/468 X |
| 4,004,583 | 1/1977 | Johnson | 297/466 X |
| 4,117,840 | 10/1978 | Rasure | 128/134 |
| 4,173,974 | 11/1979 | Belliveau | 128/133 |
| 4,359,200 | 11/1982 | Brevard et al. | 297/216 X |
| 4,360,014 | 11/1982 | Manahan | 128/134 |
| 4,488,316 | 12/1984 | Mosca | 428/100 X |
| 4,595,618 | 6/1986 | Caringer | 428/100 |
| 4,643,932 | 2/1987 | Daniels | 428/100 |
| 4,655,502 | 4/1987 | Houllis | D6/601 X |
| 4,672,910 | 6/1987 | Cook | 428/100 X |
| 4,728,553 | 3/1988 | Daniels | 428/100 |

Primary Examiner—Henry F. Epstein
Attorney, Agent, or Firm—Alan Ruderman

[57] ABSTRACT

A system for restraining the lower limbs of a prisoner being conveyed in a vehicle, such as a police car, to preclude injury to persons and to property by violent kicking action of the prisoner. The system utilizes a laminated strap having synthetic hook and loop fastening elements formed on one ply of the laminate and a reinforced vinyl backing formed on the other ply. One end of the strap is fastened to a grommet through which the other end of the strap may be drawn and folded over so that hook elements and loop elements may be engaged to adhere while the vinyl portion of the strap is tightly engaged about the lower limbs of the prisoner. A belt having a catch in the form of a buckle at one end of the belt is attached to the strap at the other end. The catch is tossed out the door of the vehicle and is lodged against a portion of the door and the adjacent door frame. The catch has a magnet bonded to a first surface thereof so that it can adhere to the vehicle and not fall away.

3 Claims, 1 Drawing Sheet

PRISONER LEG RESTRAINT

REFERENCE TO RELATED APPLICATIONS

This application is a continuation-in-part of copending application Ser. No. 07/002,212 filed Jan. 12, 1987, now U.S. Pat. No. 4,728,553, dated Mar. 1, 1988 which is a continuation-in-part of application Ser. No. 06/803,650, filed Feb. 12, 1985 now U.S. Pat. No. 4,643,932, dated Feb. 17, 1987.

BACKGROUND OF THE INVENTION

This invention relates to the restraint of the lower limbs of a prisoner to a police vehicle and more particularly to a belting system utilizing a laminated fastening strap for encircling the lower limbs of a prisoner, the belt having catch means disposed outside the vehicle to be securely tied between the door and frame of the vehicle, and the laminated strap having synthetic material fastening elements which rapidly adhere when pushed together, the fastening elements being laminated to a backing of sufficient strength to restrain the limbs of a violent prisoner.

As discussed in my aforesaid copending patent application, it is well known in the law enforcement field that substantial physical injury to an arresting officer and physical damage to public property has resulted when a suspect being taken prisoner resists arrest. Although it is notoriously well known to restrain the hands and arms of the prisoner by handcuffs or the like connecting the prisoner's hands together, in front of or behind his or her body, prior to the development of the invention in the aforesaid application, no leg restraining system has been developed which functions satisfactorily. Thus, there are many documented cases in which an arresting officer has been kicked violently as the prisoner is placed into a police cruiser, and also many more documented cases wherein the police cruiser or squad car has been badly battered by a prisoner's feet and legs as the prisoner is being driven to the station house or other detention center. In certain cases the entire partition between the police officer and the prisoner has been shattered, although most damage occurs to the doors, side panels and windows.

The use of shackles or chains to restrain the legs and feet of a prisoner is useful once a prisoner has been subdued, but such leg manacles cannot be readily placed on the prisoner and are not practical for use by an arresting officer. Moreover, unless heavily weighted they would not prevent the prisoner from lashing out with his or her feet.

Because of numerous instances in which police officers and public property have been damaged, violently acting prisoners have been restrained by other means resulting in charges of "police brutality" and, of course, costly litigation and negative publicity.

In my aforesaid copending application a lower limb restraining device is disclosed comprising an elongated strap having one ply of hook and loop fastener elements laminated to a vinyl reinforcing backing, the strap having a grommet or the like at one end through which the other end may be drawn to receive hook and loop elements together to tightly engage the strap about the limbs of a prisoner, while belting is connected to the strap and secured to an anchor within the police vehicle. Although this device functions exquisitely and is finding wide acceptance by authorities, certain authorities have raised the possibility that in the event of an accident involving the police cruiser, the prisoner could be inextricably trapped within the vehicle. It is therefore desirable to devise a prisoner restraint of this type which can be secured and released from outside the vehicle.

SUMMARY OF THE INVENTION

Consequently, it is a primary object of the present invention to provide restraining means for the lower limbs of a prisoner taken into custody by law enforcement officials, the restraining means being rapidly and securely attached about the prisoner and readily secured to the exterior of a police vehicle.

It is another object of the present invention to provide the flexible belting including a laminated fastening strap which can securely and rapidly encircle and restrain the lower limbs such as the legs, thighs or ankles of a prisoner taken into police custody, the belting including means for rapidly attaching the strap to the exterior of a police cruiser or the like between the door and door frame, to preclude violent kicking and thrashing of the prisoner's feet.

It is a further object of the present invention to provide lower limb restraining means for resisting prisoners being conveyed by a police vehicle to a station house or the like, the restraining means comprising a laminated strap having synthetic loop and fastener elements extending from a surface thereof and bonded to a strong plastic sheet of material such as reinforced vinyl, the strap being secured adjacent one end to a grommet through which the other end may be directed after encircling the lower limbs of the prisoner so that one type of fastener element may be superposed over and rapidly connected to fastener elements of the other type on the adjacent portion of the strap, the outer surfaces of the plastic sheet facing the limbs of the prisoner, and a second grommet carried by the strap for attaching one end of belting, the belting having a catch at the other end, the catch being adapted to be lodged between the door and door frame of the vehicle on the exterior thereof and preferably to adhere to the exterior surface once the belting has been tensioned to pull the catch against the vehicle.

Accordingly, the present invention provides a restraining belt means for the lower limbs of a prisoner or the like, the belt means comprising a laminated strap of the type forming the subject matter of the aforesaid U.S. Pat. No. 4,643,932 having first and second plies of material bonded together, the first ply having interconnectable plastic hook and loop fastener elements such as that sold under the trademark VELCRO bonded to a second ply of a strong pliable sheet of material such as reinforced vinyl. The hook and loop fastener elements extend from one surface of the strap so that one set of the elements may be folded back onto and adhere to the other set of elements when pressed together. One end of the strap is secured to a grommet or the like through which the other or free end of the strap may be drawn with the outer surface of the second ply folded upon itself in superposed relationship with the limbs of the prisoner therebetween. The free end of the strap may then be looped over the grommet for engaging one set of the fastener elements with the other set. One end of additional belt means is carried by the strap in either fixed relationship thereto or adjustably thereon preferably by means of a second grommet or the like, the other end of the additional belt means having an enlargement or catch adapted to be trapped rapidly between the edge of a door and the door frame or doorjamb on the exterior of a police cruiser or the like within which the prisoner is to be restrained.

Thus, a law enforcement officer after restraining the arms of a prisoner by handcuffs or the like may restrain the legs of the prisoner by looping the strap about the legs or thighs and rapidly pressing the VELCRO fastener elements together, and thereafter merely tossing the catch out the door of the prisoner compartment and rapidly slamming the door shut. A pull on the belt by the prisoner will then lodge the catch against the exterior of the vehicle.

In the preferred form of the invention the catch includes a magnet on at least one surface thereof which adheres to the police cruiser surface abutting the door edge and the frame.

BRIEF DESCRIPTION OF THE DRAWINGS

The particular features and advantages of the invention as well as other objects will become apparent from the following description taken in connection with the accompanying drawings, in which.

DESCRIPTION OF THE PREFERRED EMBODIMENT

Figure 1:
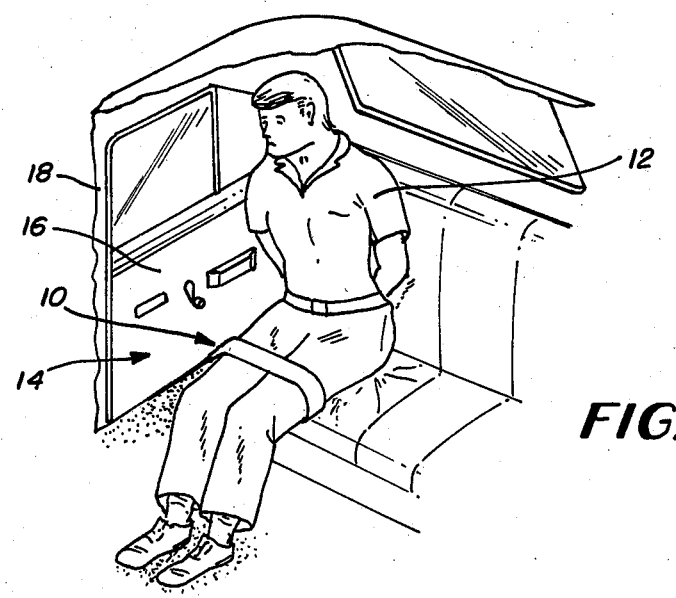
FIG. 1 is a perspective view depicting a prisoner within the prisoner compartment of a police vehicle or the like having his lower limbs restrained by restraining belt means constructed in accordance with the principles of the present invention.
Figure 2:
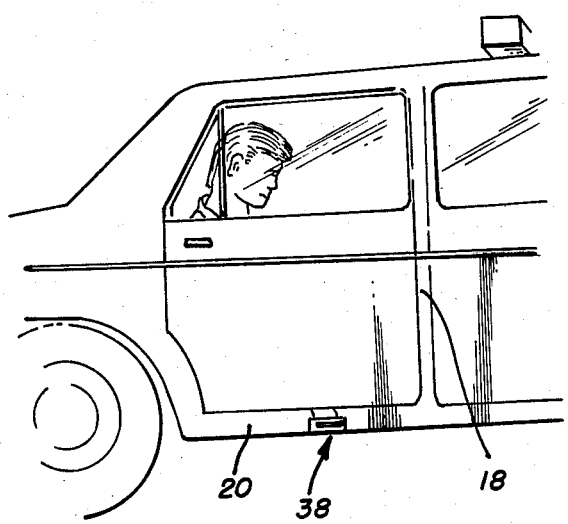
FIG. 2 is an exterior elevational view of a portion of the police vehicle illustrating the restraining catch of the restraining belt means of FIG. 1 at the outside of the vehicle.

Referring now to the drawings and particularly to FIG. 1, the restraining system 10 of the present invention is illustrated as applied to a prisoner 12 in lawful custody seated in the prisoner compartment 14 of an official vehicle while being conveyed to a police station or the like, the prisoner compartment of the vehicle having a conventional door 16 pivotably mounted on a rail or post 18 for closing within the opening of the door frame, the latter including the floor rail 20.

As conventional with regard to those disposed to violence, the arms of the prisoner are handcuffed behind his back. In the prior art it is usual for the prisoner's lower limbs, such as his legs, to be free and, if the prisoner is emotionally charged and highly violent, his feet can do great personal and physical damage. In some instances to minimize injuries the prisoner's shoes are removed. However, even if that can be accomplished by a single arresting officer without injury, for those prisoners trained in the martial arts even this is of minimal value. Thus, as pointed out in my aforesaid copending application Ser. No. 07/002,212 there has been a great need to provide law enforcement officials with a means for restraining the lower limbs of a prisoner when believed necessary. Such a restraining means must be easily and readily applied and secured by an officer in the field and in the heat of making an arrest.

As illustrated in the drawings, the present invention provides a lower limb restraining means comprising a strap 22 formed from a laminate as described in my aforesaid U.S. Pat. No. 4,643,932. On one surface of the laminate there are synthetic hook and loop fastener elements such as is known in the trade as "VELCRO" or similar material comprising a plastic sheet having a myriad of closely spaced synthetic plastic hooks 24 and loops 26 which when pushed or squeezed together interlock to form a strong connection which resists separation by a pull in the plane of the interacting parts, but which may be pulled apart by a separating pull on an end of one of the parts at an angle to the plane. A substantial longitudinally extending portion of the fastening surface of the strap preferably has the hook elements while the remainder of the strap carries the loop elements. The other surface of the laminate comprises a strong backing 28 preferably formed from reinforced vinyl, which is bonded along one surface to the rear surface of the hook and loop fastener elements, preferably along the borders of the strap, and preferably also at selected locations transverse to the borders, as described in the aforesaid U.S. Patent. Thus, a strap comprising two plies is provided wherein one of the plies comprises the "VELCRO" extending from a surface thereof and the other ply comprising a reinforced vinyl sheet, the reinforced vinyl and the bond between the two plies forming an extremely strong strap. The strap may be of any convenient length, but it has been found that a strap of approximately 45 inches in length has worked well for its intended purpose, and the length of the portion of the strap having the loops 26 being approximately 30 inches with the hooks 24 comprising at least a substantial portion of the remainder of the strap. Moreover, the strap may comprise a single length or may be formed from two laminated strips secured together, one of the strips having the hooks and the other having the loops.

Figure 3:
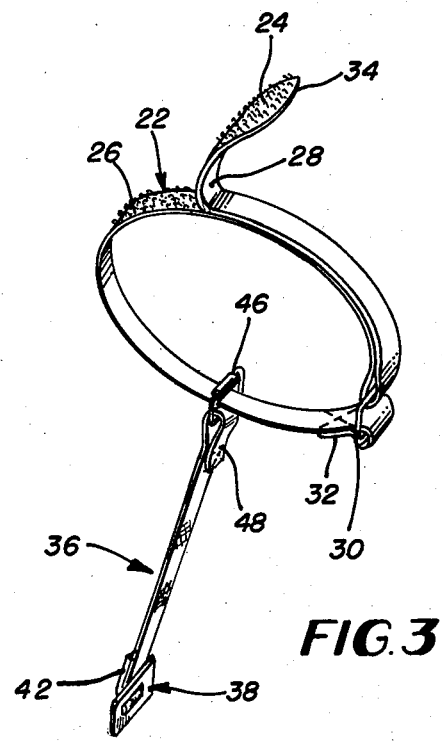
FIG. 3 is a perspective view of one form of restraining belt means constructed in accordance with the principles of the present invention.
Figure 4:
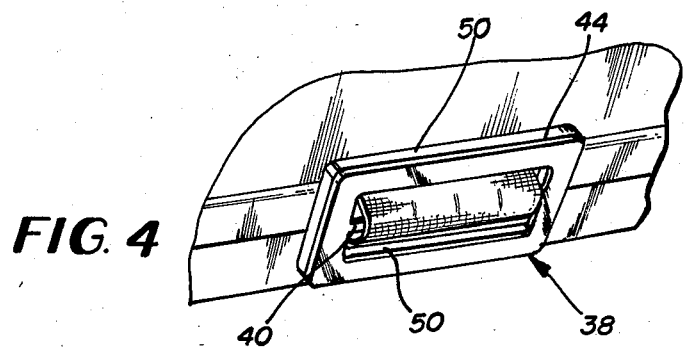
FIG. 4 is an enlarged perspective view of the catch lodged against the exterior surface of the vehicle.

As illustrated in FIG. 3 of the drawing, one end of the strap is looped about a grommet 30, folded back upon itself for a short distance as illustrated at 32 and secured to the superposed portion of the strap over which it is folded. The grommet preferably is a metal ring or any other similar type member through which the strap may be drawn. Securement may be by stitching or the like. Although either the hook or the loop end of the strap may be attached to the grommet 30 as aforesaid, the preferred end is that which carries the loop 26 as illustrated. The free end 34, i.e., the end remote from the grommet 30, may then be drawn through the grommet and folded back such that the loops 26 are disposed in facing relationship with a portion of the hooks 24. Thus, the free end 34 of the strap is folded so that the vinyl surface of the ply at the loop end faces the vinyl surface at the grommet end of the strap. The free end of the strap may thus be drawn through the grommet and folded over the grommet so that the interlinking hook and loop fastening elements of the "VELCRO" can be secured together. Accordingly, the strap may be encircled about the legs or thighs of a prisoner with only portions of the vinyl abutting the prisoner.

A second strap in the form of belting 36 has a catch member, preferably in the form of a buckle 38 or the like, secured adjacent one end thereof, the belting being connected to the strap 22 at its other end. The belting 36 may be formed from conventional belting or webbing such as utilized for automobile or airplane safety seat belts constructed from woven nylon. The buckle 38 has a central rib 40 and one end of the belt 36 may thus be disposed about the central rib, folded back over one surface of the rib and sewn to the major portion of the belt 36 as illustrated at 42. The buckle has a substantially planar rear surface 44 which contact the belt when the buckle pivots. The other end of the belt may either be fixedly or adjustably attached to the strap 18. For example, in FIG. 3 the end of the belt 36 remote from the buckle 38 may be secured about a grommet 46 or other similar ring member by stitching a folded back end portion 48 of the belt 36 in a similar manner to that at the other end. The grommet 46 is not permanently attached to the strap 22 but receives the free end of the strap and is disposed so as to freely move therealong. As stated above, the belt 36 can be fixedly secured to the end of the strap having the grommet 30 by that grommet or another through the loop formed at 32. In any case the belt 36 is of a length sufficient such that the buckle 38 may extend out the vehicle while the strap 22 is secured about the prisoner within the vehicle. Additionally, the substantially planar surface 44 of the buckle provides a surface which in use abuts the door and door frame and acts as a bearing surface to spread the load so as not to damage the vehicle.

In use, after the prisoner is handcuffed, the strap 22 may be applied about his legs or thighs prior to or as he enters the vehicle. The buckle or catch 38 may then be tossed out of the vehicle and the door 16 slammed shut. The catch will then be prevented from being pulled into the prisoner compartment as it becomes lodged against the door and the floor rail 20 or other portions of the door frame, thereby to restrain the prisoner from violently kicking his feet. In the preferred form of the invention, the catch or buckle may have a magnet 50 of similar shape to the buckle bonded to at least the rear surface 44, i.e., the surface which engages the door and frame. Thus, after the prisoner is in the vehicle and the door shut, the buckle will adhere to the door and frame at the first pulling move of the prisoner as the belt 36 slips in the space between the door and the frame. Once the buckle so adheres to and becomes attached to the metal of the door, it will not slip away from the vehicle as the prisoner relaxes. This prevents the buckle from falling from the vehicle and becoming grasped or entangled by an object when the vehicle is moving.

Numerous alterations of the structure herein disclosed will suggest themselves to those skilled in the art. However, it is to be understood that the present disclosure relates to the preferred embodiment of the invention which is for purposes of illustration only and not to be construed as a limitation of the invention. All such modifications which do not depart from the spirit of the invention are intended to be included within the scope of the appended claims.

Having thus set forth the nature of the invention, what is claimed herein is:

1. Apparatus for restraining the lower limbs of a prisoner or the like within a vehicle having a door closable within a door frame of the vehicle, said apparatus comprising an elongated laminated strap having first and second plies of material bonded together, the first ply comprising a plastic sheet having hook and loop fastener elements extending from a surface thereof, the hooks extending from a location on said sheet toward one end and the loops extending from proximate said location toward the other end, said second ply comprising a vinyl sheet of the same size as said first ply, a grommet fastened to one of said ends of said strap, the second of said ends being a free end of said strap and permitting said free end to be drawn therethrough and folded over said grommet with portions of said hook and loop elements disposed in facing relationship so as to cooperatively adhere together when engaged, whereby said strap may adjustably disposed about the lower limbs of said prisoner to lock said limbs together, and a belt of finite length having a first end connected to said strap and having a catch secured at another end, said length being sufficient such that the catch may be disposed outside the vehicle when the prisoner is within the vehicle, said catch being of a size not to slip between said door and said frame when the door is shut.

2. Apparatus as recited in claim 1, wherein said catch has a substantially planar surface for bearing against said door and adjacent portions of the door frame when said belt is pulled into the vehicle.

3. Apparatus as recited in claim 2, wherein said substantially planar surface includes a magnet secured thereto for adhering to said door and frame.

* * * * *